(12) United States Patent
Maurin et al.

(10) Patent No.: US 6,562,772 B1
(45) Date of Patent: May 13, 2003

(54) COMPOSITION FOR WASHING KERATIN MATERIALS, BASED ON A DETERGENT SURFACTANT, A NACREOUS AND/OR OPACIFYING AGENT AND AN ACRYLIC TERPOLYMER

(75) Inventors: Veronique Maurin, Paris (FR); Bernard Beauquey, Clichy (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/671,191

(22) Filed: Sep. 28, 2000

(30) Foreign Application Priority Data

Sep. 29, 1999 (FR) ............................................. 99 12169

(51) Int. Cl.⁷ .............................. C11D 1/83; C11D 1/94; C11D 3/26; C11D 3/37
(52) U.S. Cl. ........................ 510/124; 510/123; 510/125; 510/127; 510/130; 510/158; 510/159; 510/499; 510/505; 510/475
(58) Field of Search ................................. 510/123, 124, 510/125, 127, 130, 158, 159, 499, 505, 475; 424/70.16, 70.17, 70.22, 70.28, 70.31

(56) References Cited

U.S. PATENT DOCUMENTS 6,025,431 A * 2/2000 Cardinali et al. ........... 525/547
6,096,697 A * 8/2000 Wells .......................... 510/127
6,106,815 A * 8/2000 Kang et al. ............... 424/70.12
6,191,083 B1 * 2/2001 Brooks et al. .............. 510/124

* cited by examiner

Primary Examiner—Gregory Delcotto
(74) Attorney, Agent, or Firm—Jacobson Holman PLLC

(57) ABSTRACT

A composition for washing keratin materials combines in a cosmetically acceptable medium:

i) at least one anionic, amphoteric or nonionic detergent surfactant;

ii) at least 1.5% by weight, relative to the total weight of the composition, of a nacreous and/or opacifying agent; and iii) at least one acrylic terpolymer made from a monomer (a) chosen from a $C_1$–$C_6$ alkyl acrylate and a $C_1$–$C_6$ alkyl methacrylate; of a monomer (b) chosen from a heterocyclic vinyl compound containing at least one nitrogen or sulphur atom, a (meth)acrylamide, a mono- or di($C_1$–$C_4$)alkylamino($C_1$–$C_4$)alkyl (meth)acrylate and a mono- or di($C_1$–$C_4$)alkylamino($C_1$–$C_4$)alkyl (meth)acrylamide; of a monomer (c) chosen from a urethane produced by reaction between a monoethylenic unsaturated isocyanate and a nonionic surfactant, a copolymerizable ethylenic surfactant monomer, a surfactant monomer of urea type, an allyl ether containing alkylenoxy groups and a nonionic monomer of urethane type.

41 Claims, No Drawings

COMPOSITION FOR WASHING KERATIN MATERIALS, BASED ON A DETERGENT SURFACTANT, A NACREOUS AND/OR OPACIFYING AGENT AND AN ACRYLIC TERPOLYMER

The present invention relates in general to compositions for washing keratin materials, based on a detergent surfactant, a nacreous and/or opacifying agent and an acrylic terpolymer, as well as to a washing process using these compositions.

Nacreous and/or opacifying agents are commonly used in shampoos in order to give these shampoos a nacreous appearance, which is preferred by consumers. It has been found that, due to the low density of these nacreous agents, they often have the drawback of rising to the surface of the shampoo and forming a layer thereat, which consumers find aesthetically unpleasant. Polymers, in particular crosslinked acrylic acid such as Carbopols, are frequently used to avoid the appearance of this phenomenon; however, they have the drawback of reducing the cosmetic performance qualities of shampoos, in particular by making keratin fibres coarser and more charged.

There is thus a need for a detergent cosmetic composition, in particular a shampoo, which has a nacreous and/or opacified appearance while at the same time giving acceptable cosmetic performance qualities on keratin materials, i.e. in particular the hair and the scalp; and more particularly as regards the lightness, softness and feel of the hair.

The Applicant has discovered, surprisingly, that it is possible to formulate compositions for washing keratin materials, in particular shampoos with a nacreous and/or opacified appearance while at the same time having the desired aesthetic and cosmetic properties, by using in these compositions a detergent surfactant and a nacreous and/or opacifying agent combined with a specific acrylic terpolymer, defined below. Specifically, it has been found that the use of the said acrylic terpolymer gives keratin materials, and in particular the hair, satisfactory cosmetic properties, particularly by making them lighter and by making wet hair feel soft and by giving dried hair greater softness, smoothness, suppleness, manageability and sheen.

It has also been found that the compositions according to the invention have good solubility and good skin tolerance.

A subject of the invention is thus compositions for washing keratin materials, essentially characterized in that they comprise, in a cosmetically acceptable medium:
1) at least one anionic, amphoteric or nonionic detergent surfactant;
2) at least 1.5% by weight, relative to the total weight of the composition, of at least one nacreous and/or opacifying agent chosen from:
   i) esters of polyols containing more than two carbon atoms and of long-chain fatty acids;
   ii) long-chain fatty acid alkanolamides;
   iii) esters of long-chain monoalcohols and of long-chain fatty acids;
   iv) long-chain fatty alkyl ethers;
   v) long-chain esters of long-chain alkanolamides;
   vi) single-chain fatty alcohols containing more than 20 carbon atoms;
   vii) long-chain amine oxides;
   viii) N,N-dihydrocarbyl($C_{10}$–$C_{30}$, preferably $C_{12}$–$C_{22}$) amidobenzoic acid and their salts;
   ix) alcohols containing from 27 to 48 carbon atoms and comprising one or two ether and/or thioether or sulphoxide groups; and
   x) titanium oxides and micas;
3) and at least one acrylic terpolymer consisting of:
   from 5% to 80% by weight, preferably from 15% to 70% by weight and more preferably from 40% to 70% by weight, of an acrylate monomer (a) chosen from a $C_1$–$C_6$ alkyl acrylate and a $C_1$–$C_6$ alkyl methacrylate;
   from 5% to 80% by weight, preferably from 10% to 70% by weight and more preferably from 20% to 60% by weight, of a monomer (b) chosen from a heterocyclic vinyl compound containing at least one nitrogen or sulphur atom, a (meth)acrylamide, a mono- or di($C_1$–$C_4$)alkylamino($C_1$–$C_4$)alkyl (meth)acrylate and a mono- or di($C_1$–$C_4$)alkylamino($C_1$–$C_4$)alkyl(meth)acrylamide;
   from 0.1% to 30% by weight, preferably from 0.1% to 10% by weight, of a monomer (c) chosen from:
   a urethane produced by reaction between a monoethylenic unsaturated isocyanate and a nonionic surfactant encompassing a block copolymer of 1,2-butylene oxide and of ethylene oxide containing a $C_{1-4}$ alkoxy end;
   a copolymerizable ethylenic unsaturated surfactant monomer obtained by condensing a nonionic surfactant with an α, β-ethylenic unsaturated carboxylic acid or its anhydride;
   a surfactant monomer chosen from reaction products such as urea of a monoethylenic unsaturated monoisocyanate with a nonionic surfactant containing an amine function;
   a (meth)allyl ether of formula $CH_2=CR_1CH_2OA_mB_nA_pR_2$ in which $R_1$ denotes a hydrogen atom or a methyl group, A denotes a propylenoxy or butylenoxy group, B denotes ethylenoxy, n is equal to zero or denotes an integer less than or equal to 200 and preferably less than 100, m and p denote zero or an integer less than n and $R_2$ is a hydrophobic group of at least 8 carbon atoms and preferably of $C_8$–$C_{30}$; and
   a nonionic monomer such as urethane produced by reaction of a monohydric nonionic surfactant with a monoethylenic unsaturated isocyanate; the weight percentages of monomers being based on the total weight of the monomers constituting the terpolymer.

In the washing composition according to the invention, the acrylic terpolymer is present in a proportion of from 0.01% to 20% by weight of active material (A.M.), preferably 0.1% to 10% by weight, relative to the total weight of the composition.

Preferred acrylate monomers (a) in particular comprise $C_2$–$C_6$ alkyl acrylates. Ethyl acrylate is most particularly preferred.

Examples of preferred monomers (b) which may be mentioned are N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylaminopropylacrylamide, N,N-dimethylaminopropylmethacrylamide, N,N-diethylaminopropylacrylamide and N,N-diethylaminopropylmethacrylamide. N,N-Dimethylaminoethyl methacrylate is most particularly preferred.

The preferred monomers (c) are the copolymerizable ethylenic unsaturated surfactant monomers obtained by condensing a nonionic surfactant with an α, β-ethylenic unsaturated carboxylic acid or its anhydride, preferably $C_3$–$C_4$ mono- or dicarboxylic acids or their anhydrides and more particularly acrylic acid, methacrylic acid, crotonic acid, maleic acid, maleic anhydride and most particularly itaconic acid and itaconic anhydride.

The monomers (c) that are particularly preferred correspond to the copolymerizable ethylenic unsaturated surfactant monomers obtained by condensing a nonionic surfactant with itaconic acid. Among the nonionic surfactants which may be mentioned in particular are $C_{10}$–$C_{30}$ fatty alcohols alkoxylated with 2 to 100 mol and preferably from 5 to 50 mol of an alkylene oxide, such as, for example, polyethylene glycol ethers of $C_{10}$–$C_{30}$ fatty alcohols and more particularly the polyethylene glycol ethers of cetyl alcohol which are known as Ceteth in the CTFA dictionary, 7th edition, 1997.

Conventional methods for preparing these acrylic terpolymers are known to those skilled in the art. Such methods include solution polymerization, precipitation polymerization and emulsion polymerization, for example. Terpolymers in accordance with the invention and methods for preparing them are described in particular in patent applications EP-A-0 824 914 and EP-A-0 825 200.

Among these terpolymers, it is preferred in particular to use the <<Structure® Plus>> polymer sold by the company National Starch, which consists of acrylates, amino(meth)acrylates and $C_{10}$–$C_{30}$ alkyl itaconate, polyoxyethylenated with 20 mol of ethylene oxide, in the form of an aqueous dispersion containing 20% A.M.

In addition to these monomers, the terpolymer can contain other monomers which allow the said terpolymer to be crosslinked. These monomers are used in relatively low proportions, of up to 2% by weight relative to the total weight of the monomers used to prepare the terpolymer. Such crosslinking monomers comprise aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes. Crosslinking monomers may be, in particular, divinylbenzenes, trivinylbenzenes, 1,2,4-trivinylcyclohexene, 1,5-hexadiene, 1,5,9-decatriene, 1,9-decadiene, 1,5-heptadiene, diallyl phthalates, ethylene glycol dimethacrylates, polyethylene glycol dimethacrylates, penta- and tetraacrylates, triallyl pentaerythritols, octaallyl sucroses, cycloparaffins, cycloolefins and N-methylenebisacrylamide.

The nacreous and/or opacifying agents of the invention are chosen from:
i) esters of polyols containing more than two carbon atoms and of long-chain, preferably $C_{10}$–$C_{30}$ and even more preferably $C_{16}$–$C_{22}$, fatty acids;
ii) long-chain, preferably $C_{10}$–$C_{30}$ and even more preferably $C_{16}$–$C_{22}$, fatty acid alkanolamides, such as stearic monoethanolamide, stearic diethanolamide, stearic monoisopropanolamide or stearic monoethanolamide stearate;
iii) esters of long-chain ($C_{10}$–$C_{30}$) monoalcohols and of long-chain ($C_{10}$–$C_{30}$) fatty acids, such as cetyl palmitate;
iv) long-chain fatty alkyl ethers that are solid at a temperature of less than or equal to 30° C., such as, for example, the dialkyl ethers of formula (I): R—O—R' (I) in which R and R', which may be identical or different, denote a saturated or unsaturated, linear or branched alkyl radical containing from 10 to 30 carbon atoms and preferably from 14 to 24 carbon atoms, R and R' being chosen such that the compound of formula (I) is solid at a temperature of less than or equal to 30° C. More particularly, R and R' denote a stearyl radical. These compounds can be prepared in particular according to the process described in patent application DE 41 27 230. One distearyl ether which can be used in the context of the present invention is sold under the name Cutina STE by the company Henkel;
v) long-chain ($C_{10}$–$C_{30}$) esters of long-chain ($C_{10}$–$C_{30}$) alkanolamides, such as stearamide diethanolamide distearate or stearamide monoethanolamide stearate;
vi) single-chain fatty alcohols containing more than 20 carbon atoms, such as behenyl alcohol;
vii) long-chain amine oxides, such as ($C_{10}$–$C_{30}$) alkyldimethylamine oxides, such as, for example, stearyldimethylamine oxide;
viii) N,N-dihydrocarbyl ($C_{10}$–$C_{30}$, preferably $C_{12}$–$C_{22}$) amidobenzoic acids and their salts, and particularly N,N-di ($C_{16}$–$C_{18}$)amidobenzoic acid sold by the company Stefan Company; and
ix) alcohols containing from 27 to 48 carbon atoms and comprising one or two ether and/or thioether or sulphoxide groups, corresponding to formula (II):

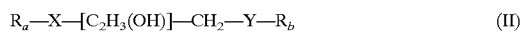

$$R_a\text{—}X\text{—}[C_2H_3(OH)]\text{—}CH_2\text{—}Y\text{—}R_b \qquad (II)$$

in which
$R_a$ and $R_b$ denote, independently of each other, linear $C_{12}$ to $C_{24}$ groups;
X denotes an oxygen atom, a sulphur atom or a sulphoxide or methylene group;
Y denotes an oxygen atom, a sulphur atom or a sulphoxide or methylene group;
the sum of the number of carbon atoms present in the groups $R_a$ and $R_b$ has a value ranging from 24 to 44 and preferably from 28 to 40 inclusive;
when X or Y denotes sulphoxide, Y or X does not denote sulphur.

The compounds of formula (II) preferably used in accordance with the invention are those for which X denotes oxygen, Y denotes methylene and $R_a$ and $R_b$ denote radicals containing 12 to 22 carbon atoms, it being possible for these compounds to be prepared according to patent EP 457 688; and
x) coated or uncoated titanium oxides, micas and titanium micas.

The nacreous and/or opacifying agents are chosen preferably from distearyl ether, behenyl alcohol and 1-(hexadecyloxy)-2-octadecanol.

At least one nacreous and/or opacifying agent should be present in proportions of at least 1.5% by weight, and preferably in proportions of between 1.5% and 20% and even more preferably between 2% and 6% by weight, relative to the total weight of the composition. These proportions are necessary in order to obtain a composition which has a nacreous and/or opacified appearance.

As mentioned previously, the compositions according to the invention contain at least one detergent surfactant, chosen from anionic, amphoteric and nonionic surfactants with detergent properties, and mixtures thereof.

Among the anionic surfactants which may be mentioned are alkaline salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkyl sulphonates, alkylamide sulphonates, alkylaryl sulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates, alkyl ether phosphates; acyl sarcosinates, acyl isethionates and N-acyl taurates.

The alkyl or acyl radical in these various compounds generally consists of a carbon-based chain containing from 8 to 30 carbon atoms.

Among the anionic surfactants which may also be mentioned are fatty acid salts such as oleic, ricinoleic, palmitic and stearic acid salts; coconut oil acid or hydrogenated coconut oil acid; acyl lactylates, in which the acyl radical contains from 8 to 30 carbon atoms.

Surfactants considered as weakly anionic can also be used, such as polyoxyalkylenated carboxylic alkyl or alkylaryl ether acids or salts thereof, polyoxyalkylenated carboxylic alkylamido ether acids or salts thereof, and alkyl D-galactosiduronic acids or salts thereof.

The nonionic surfactants are chosen more particularly from polyethoxylated, polypropoxylated or polyglycerolated fatty acids or alkylphenols or alcohols, with a fatty chain containing 8 to 30 carbon atoms, the number of ethylene oxide or propylene oxide groups being between 2 and 50 and the number of glycerol groups being between 2 and 30.

Mention may also be made of copolymers of ethylene oxide and propylene oxide; condensates of ethylene oxide and of propylene oxide with fatty alcohols; polyethoxylated fatty amides preferably containing 2 to 30 mol of ethylene oxide; polyglycerolated fatty amides preferably comprising 1 to 5 and in particular 1.5 to 4 glycerol groups; polyethoxylated fatty amines preferably containing 2 to 30 mol of ethylene oxide; oxyethylenated fatty acid esters of sorbitan with 2 to 30 mol of ethylene oxide; fatty acid esters of sucrose, fatty acid esters of polyethylene glycol, alkylpolyglycosides, carbamate or amide derivatives of N-alkylglucamines, aldobionamides, amine oxides such as alkylamine oxides or of N-acylamidopropylmorpholine.

The preferred amphoteric surfactants are secondary or tertiary aliphatic amine derivatives, in which the aliphatic radical is a linear or branched chain containing 8 to 22 carbon atoms and which contains at least one carboxylate, sulphonate, sulphate, phosphate or phosphonate water-solubilizing anionic group; $(C_8-C_{20})$alkylbetaines, sulphobetaines, $(C_8-C_{20})$alkylamido $(C_1-C_6)$alkylbetaines or $(C_8-C_{20})$alkylamido $(C_1-C_6)$alkylsulphobetaines.

Among the amine derivatives which may be mentioned are the products sold under the name Miranol, such as those described in patents U.S. Pat. Nos. 2,528,378 and 2,781,354 and classified in the CTFA dictionary, 7th edition, 1997, under the name Disodium Cocoamphodiacetate, Disodium Lauroamphodiacetate, Disodium Caprylamphodiacetate, Disodium Caproamphodiacetate, Disodium Cocoamphodipropionate, Disodium Lauroamphodipropionate, Disodium Caproamphodipropionate, Disodium Caprylamphodipropionate, Lauroamphodipropionate acid, Cocoamphodipropionate acid.

The surfactants are used in the compositions in accordance with the invention in proportions that are sufficient to give the composition a detergent nature, generally in a proportion of at least 4% by weight, preferably between 5% and 50% by weight, relative to the total weight of the composition and in particular between 8% and 35%.

The compositions according to the invention have a pH generally of between 3 and 12 and more particularly between 4 and 8.

The cosmetically acceptable medium for the compositions consists either of water or of one or more solvents or of a mixture of water and at least one cosmetically acceptable solvent chosen from lower alcohols, alkylene glycols and polyol ethers.

According to one preferred embodiment of the invention, the compositions according to the present invention contain modified or unmodified polyorganosiloxanes, i.e. polyorganosiloxane oils or polyorganosiloxane gums or resins, in their native form or in the form of solutions in organic solvents or alternatively in the form of emulsions or microemulsions.

Among the polyorganosiloxanes which can be used in accordance with the present invention, mention may be made, in a non-limiting manner, of:

I. Volatile silicones: these have a boiling point of between 60° C. and 260° C. They are chosen from cyclic silicones containing from 3 to 7 and preferably 4 to 5 silicon atoms. Examples of these silicones are octamethylcyclotetrasiloxane sold under the name <<Volatile Silicone 7207>> by Union Carbide or <<Silicone 70045 V2>> by Rhodia Chimie, decamethylcyclopentasiloxane sold under the name <<Volatile Silicone 7158>> by Union Carbide and <<Silicone 70045 V5>> by Rhodia Chimie, as well as mixtures thereof. Mention is also made of cyclocopolymers of the dimethylsiloxane/methylalkylsiloxane type, such as <<Volatile Silicone FZ3109>> sold by the company Union Carbide, which is a dimethylsiloxane/methyloctylsiloxane cyclocopolymer.

II. Non-volatile silicones: these consist mainly of:
  (i) polyalkylsiloxanes; among the polyalkylsiloxanes which may mainly be mentioned are linear polydimethylsiloxanes containing trimethylsilyl end groups, such as, for example, and in a non-limiting manner, the <<Silbione>> oils of the 70047 series sold by Rhône Poulenc;
  (ii) polyarylsiloxanes;
  (iii) polyalkylarylsiloxanes; mention may be made of linear and branched polymethylphenylsiloxanes, polydimethylmethylphenylsiloxanes and polydimethyldiphenylsiloxanes, such as, for example, the oil <<Rhodorsil 763>> from Rhodia Chimie;
  (iv) silicone gums; these are polydiorganosiloxanes with a molecular mass of between 200,000 and 1,000,000, which are used alone or as a mixture in a solvent chosen from volatile silicones, polydimethylsiloxane (PDMS) oils, polyphenylmethylsiloxane (PPMS) oils, isoparaffins, methylene chloride, pentane, dodecane, tridecane and tetradecane, or mixtures thereof; they can have structures of the type:
  polydimethylsiloxane,
  poly[(dimethylsiloxane)/(methylvinylsiloxane)],
  poly[(dimethylsiloxane)/(diphenylsiloxane)],
  poly[(dimethylsiloxane)/(phenylmethylsiloxane)],
  poly[(dimethylsiloxane)/(diphenylsiloxane)/(methylvinylsiloxane)];
  mention may also be made, by way of example, and in a non-limiting manner, of the following mixtures:
   1) mixtures formed from a polydimethylsiloxane hydroxylated at the end of the chain (Dimethiconol according to the CTFA nomenclature) and from a cyclic polydimethylsiloxane (Cyclomethicone according to the CTFA nomenclature), such as the product <<Q2 1401>> sold by the company Dow Corning;
   2) mixtures formed from a polydimethylsiloxane gum with a cyclic silicone, such as the product <<SF 1214 Silicone Fluid>> from General Electric, which is an SE 30 gum of MW 500,000 dissolved in <<SF 1202 Silicone Fluid>> (decamethylcyclopentasiloxane);
   3) mixtures of two PDMSs of different viscosity, in particular of a PDMS gum and of a PDMS oil, such as the products <<SF 1236>> and <<CF 1241>> from the company General Electric;

(v) silicone resins; preferably crosslinked siloxane systems containing $R_2SiO_{2/2}$, $RSiO_{3/2}$ and $Si_{4/2}$ units in which R represents a hydrocarbon group containing 1 to 6 carbon atoms or a phenyl group. Among these resins, mention may be made of the product sold under the name <<Dow Corning 593>>;

(vi) organomodified polyorganosiloxanes; i.e. silicones as defined above, comprising in their general structure one or more organofunctional groups directly linked to the siloxane chain or linked via a hydrocarbon-based radical; mention is made, for example, of silicones comprising:

a) polyethylenoxy and/or polypropylenoxy groups optionally comprising alkyl groups, such as the product known as dimethicone copolyol sold by the company Dow Corning under the name <<DC 1248>> and the alkyl (C12) methicone copolyol sold by the company Dow Corning under the name <<Q2 5200>>;

b) (per)fluoro groups, such as trifluoroalkyl groups, such as, for example, those sold by the company General Electric under the name <<FF.150 Fluorosilicone Fluid>>;

c) hydroxyacylamino groups, such as those described in European patent application EP-A-0 342 834 and in particular the silicone sold by the company Dow Corning under the name <<Q2-8413>>;

d) thiol groups, such as in the silicones <<X 2-8360>> from Dow Corning or –<GP 72A>> and <<GP 71>> from Genesee;

e) substituted or unsubstituted amine groups, such as the products sold under the name GP 4 Silicone Fluid and GP 7100 by the company Genesee or the products sold under the names Q2 8220 and Dow Corning 929 or 939 by the company Dow Corning. The substituted amine groups are, in particular, $C_1$–$C_4$ aminoalkyl or amino($C_1$–$C_4$)alkylamino($C_1$–$C_4$) alkyl groups. The silicones known as amodimethicone and trimethylsilylamodimethicone according to the CTFA name (1997) are used more particularly;

f) carboxylate groups, such as the products described in European patent EP 186 507 from Chisso Corporation;

g) hydroxyl groups, such as the polyorganosiloxanes containing a hydroxyalkyl function, which are described in patent application FR-A-2 589 476;

h) alkoxy groups containing at least 12 carbon atoms, such as the product <<Silicone Copolymer F 755>> from SWS Silicones;

i) acyloxyalkyl groups containing at least 12 carbon atoms, such as, for example, the polyorganosiloxanes described in patent application FR-A-2 641 185;

j) quaternary ammonium groups, such as in the product <<Abil K 3270>> from the company Goldschmidt;

k) amphoteric or betaine groups, such as in the product sold by the company Goldschmidt under the name <<Abil B 9950>>;

l) bisulphite groups, such as in the products sold by the company Goldschmidt under the names <<Abil S 201>> and <<Abil S 255>>;

(vii) block copolymers containing a linear polysiloxane-polyalkylene block as repeating unit; the preparation of such block copolymers used in the context of the present invention is described in European patent application EP 0 492 657 A1, the teaching of which is included in the present description by way of reference;

(viii) grafted silicone polymers, containing a non-silicone organic skeleton, consisting of a main organic chain formed from organic monomers containing no silicone, onto which is grafted, inside the said chain as well as, optionally, on at least one of its ends, at least one polysiloxane macromonomer; in particular those chosen more preferably from those described in U.S. Pat. Nos. 4,963,935, 4,728,571 and 4,972,037 and patent applications EP-A-0 412 704, EP-A-0 412 707, EP-A-0 640 105 and WO 95/00578, the teachings of which are included in their entirety into the present description by way of non-limiting references;

(ix) grafted silicone polymers, containing a polysiloxane skeleton grafted with non-silicone organic monomers, comprising a main polysiloxane chain onto which is grafted, within the said chain as well as, optionally, on at least one of its ends, at least one organic macromonomer containing no silicone; examples of such polymers, as well as the particular method for preparing them, are described in particular in patent applications EP-A-0 582 152, WO 93/23009 and WO 95/03776, the teachings of which are included in their entirety into the present description by way of non-limiting references;

(x) or mixtures thereof.

The polyorganosiloxanes preferably used according to the invention are the aminated or non-aminated non-volatile polydimethylsiloxanes.

The polyorganosiloxanes are used in the compositions of the invention in proportions of between 0.01% and 20% by weight and preferably between 0.1% and 10% by weight relative to the total weight of the composition.

In another preferred embodiment, the compositions of the invention also contain at least one cationic polymer chosen from all those already known per se, in particular those described in patent application EP-A-0 337 354 and in French patent applications FR-A-2 270 846, 2 383 660, 2 598 611, 2 470 596 and 2 519 863.

The cationic polymers used generally have a molecular mass of between 500 and 5 $10^6$ approximately and preferably between $10^3$ and 3 $10^6$ approximately.

Among the cationic polymers which may be mentioned more particularly are quaternized proteins (or protein hydrolysates) and polymers of the polyamine, polyaminoamide and polyguaternary ammonium type. These are known products.

The quaternized proteins or protein hydrolysates are in particular chemically modified polypeptides bearing quaternary ammonium groups at the end of a chain, or grafted onto this chain. Their molecular mass can vary, for example, from 1500 to 10,000, and in particular from 2000 to 5000 approximately. Among these compounds, mention may be made in particular of:

collagen hydrolysates bearing triethylammonium groups, such as the products known in the CTFA dictionary as <<Triethonium Hydrolysed Collagen Ethosulphate>>;

collagen hydrolysates bearing trimethylammonium chloride and trimethylstearylammonium chloride groups, which are known in the CTFA dictionary as <<Steartrimonium Hydrolysed Collagen>>;

protein hydrolysates bearing on the polypeptide chain quaternary ammonium groups comprising at least one alkyl radical containing from 1 to 18 carbon atoms.

Among these protein hydrolysates which may be mentioned, inter alia, are <<Croquat L>>, <<Croquat M>>, <<Croquat S>> and <<Crotein Q>> sold by the company Croda.

Other quaternized proteins or hydrolysates are, for example, those sold by the company Inolex, under the name <<Lexein QX 3000>>.

Mention may also be made of quaternized plant proteins such as wheat, corn or soybean proteins: quaternized wheat proteins which may be mentioned are those known in the CTFA dictionary as <<Cocodimonium Hydrolysed Wheat Protein>>, <<Lauridimonium Hydrolysed Wheat Protein>> or <<Steardimonium Hydrolysed Wheat Protein>>.

The polymers of the polyamine, polyaminoamide or polyquaternary ammonium type which may be used in accordance with the present invention and which may be mentioned in particular are those described in French patents Nos. 2 505 348 and 2 542 997. Among these polymers, mention may be made of:

(1) Quaternized or non-quaternized vinylpyrrolidone/dialkylaminoalkyl acrylate or methacrylate copolymers, such as the polymers described in detail in French patents 2 077 143 and 2 393 573.

(2) Cellulose ether derivatives comprising quaternary ammonium groups, described in French patent 1 492 597.

(3) Cationic cellulose derivatives such as cellulose copolymers or cellulose derivatives grafted with a water-soluble quaternary ammonium monomer, and described in particular in U.S. Pat. No. 4,131,576, such as hydroxyalkylcelluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt.

(4) Polysaccharides and in particular cationic guar gums described more particularly in U.S. Pat. Nos. 3,589,578 and 4,031,307.

(5) Polymers consisting of piperazinyl units and of divalent alkylene or hydroxyalkylene radicals containing straight or branched chains, optionally interrupted with oxygen, sulphur or nitrogen atoms or with aromatic or heterocyclic rings, as well as the oxidation and/or quaternization products of these polymers. Such polymers are described in particular in French patents 2 162 025 and 2 280 361.

(6) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or with an oligomer resulting from the reaction of a bifunctional compound which is reactive towards a bis-halohydrin, a bis-azetidinium, a bis-haloacyldiamine, a bis-alkyl halide, an epihalohydrin, a diepoxide or a bis-unsaturated derivative, the crosslinking agent being used in proportions ranging from 0.025 to 0.35 mol per amine group of the polyaminoamide; these polyaminoamides can be alkylated or, if they comprise one or more tertiary amine functions, they can be quaternized. Such polymers are described in particular in French patents 2 252 840 and 2 368 508.

(7) Polyaminoamide derivatives resulting from the condensation of polyalkylene polyamines with polycarboxylic acids followed by an alkylation with bifunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1 583 363.

(8) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms, the molar ratio between the polyalkylene polyamine and the dicarboxylic acid being between 0.8:1 and 1.4:1, the polyaminoamide resulting therefrom being reacted with the epichlorohydrin in a molar ratio of epichlorohydrin relative to the secondary amine group of the polyaminoamide of between 0.5:1 and 1.8:1. Such polymers are described in particular in U.S. Pat. Nos. 3,227,615 and 2,961,347.

(9) Cyclopolymers of methyldiallylamine or of dimethyldiallylammonium, in particular those described in French patent 2 080 759 and in its Certificate of Addition 2 190 406.

(10) The diquaternary ammonium polymers described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,02, 2,271,378, 3,874,870, 4,001,432, 3,929,990, 3,966,904, 4,005,193, 4,025,617, 4,025,627, 4,025,653, 4,026,945 and 4,027,020.

(11) The polyquaternary ammonium polymers described in particular in patent application EP-A-122 324.

(12) Homopolymers or copolymers derived from acrylic or methacrylic acids and comprising $CH_2$—$CHR_a$—$CO$—$O$—$A_1$—$NR_eR_f$, $CH_2$—$CHR$—$CO$—$O$—$A_1$—$N^+R_bR_cR_d$, $X^-$ and/or $CH_2$—$CHR_a$—$CO$—$NH$—$A_1$—$N^+R_bR_cR_d$, $X^-$ units, in which the groups $R_a$ independently denote H or $CH_3$, the groups $A_1$ independently denote a linear or branched alkyl group of 1 to 6 carbon atoms or a hydroxyalkyl group of 1 to 4 carbon atoms, the groups $R_b$, $R_c$, and $R_d$, which may be identical or different, independently denote an alkyl group of 1 to 18 carbon atoms or a benzyl radical, the groups $R_e$ and $R_f$ represent a hydrogen atom or an alkyl group of 1 to 6 carbon atoms, $X^-$ denotes an anion, for example methosulphate or halide, such as chloride or bromide

(13) Quaternary polymers of vinylpyrrolidone and of vinylimidazole such as, for example, the products sold under the names <<Luviquat FC 905>>, <<Luviquat FC 550>> and <<Luviquat FC 370>> by the company BASF.

(14) The polyamines such as <<Polyquart H>> sold by Henkel, referred to under the name <<Polyethylene Glycol Tallow Polyamine>> in the CTFA dictionary.

(15) Crosslinked polymers of methacryloyloxyethyltrimethylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by a crosslinking with a compound containing olefinic unsaturation, in particular methylenebisacrylamide. An acrylamide/methacryloyloxyethyltrimethylammonium chloride crosslinked copolymer (20/80 by weight) in the form of a dispersion containing 50% by weight of the said copolymer in mineral oil can more particularly be used.

Other cationic polymers which can be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers which can be used in the context of the present invention, cellulose ether derivatives comprising quaternary ammonium groups, polysaccharides and in particular cationic guar gum and cyclopolymers of methyldiallylamine or of dimethyldiallylammonium are preferred.

The cationic polymers are used in the compositions of the invention in proportions of between 0.001% and 20% by weight and preferably between 0.05% and 5% by weight, relative to the total weight of the composition.

According to one particularly preferred embodiment, the compositions of the invention also contain at least one silicone and at least one cationic polymer.

The compositions according to the invention can furthermore also contain at least one adjuvant chosen from the adjuvants usually used in cosmetics, such as fragrances, preserving agents, sequestering agents, wetting agents, sugars, plant, animal, mineral or synthetic oils, amphoteric polymers, cationic surfactants, menthol, nicotinate derivatives, agents for preventing hair loss, antidandruff agents, and foam stabilizers, propellants, screening agents, dyes, ceramides, vitamins or provitamins, and acidifying or basifying agents.

In one preferred embodiment of the invention, the compositions according to the invention are used as shampoos for washing and treating the hair.

The process for washing keratin materials consists in applying a composition as defined above to wet or dry keratin materials in amounts that are effective to wash them, this application being followed by rinsing after an optional period of leaving the composition to stand on the keratin materials.

The examples which follow are intended to illustrate the invention.

EXAMPLE I
Shampoo

| | |
|---|---|
| Cocoyl betaine as an aqueous 30% solution | 8 g |
| Hydroxypropyl guar trimethyl ammonium chloride sold by the company Meyhall under the name «Jaguar C13S» | 0.05 g |
| Polydimethylsiloxane with a viscosity of 0.3 m².s⁻¹, sold by the company Dow Corning under the name «DC 200 Fluid 300,000» | 2.7 g |
| 1-(Hexadecyloxy)-2-octadecanol/cetyl alcohol mixture | 2.5 g |
| Coconut acid monoisopropanolamide | 0.5 g |
| Sodium lauryl ether sulphate (2.2 EO) containing 70% A.M. | 22 g |
| Terpolymer of acrylates, amino(meth)acrylates and $C_{10}$–$C_{30}$ alkyl itaconate, polyoxyethylenated with 20 mol of ethylene oxide, in the form of an aqueous dispersion containing 20% A.M., sold by the company National Starch under the name «Structure ® Plus» | 1 g |
| Fragrance, preserving agents | qs |
| Sterilized demineralized water | qs 100 g |

The pH is adjusted to 7.5 with citric acid or sodium hydroxide.

After using this shampoo, wet hair is found to have softness and dried hair is found to have softness, sheen, a smooth feel, suppleness and good manageability.

EXAMPLE II
Shampoo

| | |
|---|---|
| Propylene glycol | 0.1 g |
| Cocoyl betaine as an aqueous 30% solution | 10 g |
| Hydroxypropyl guar trimethyl ammonium chloride sold by the company Meyhall under the name «Jaguar C13S» | 0.1 g |
| 1-(Hexadecyloxy)-2-octadecanol/cetyl alcohol mixture | 2.5 g |
| Coconut acid monoisopropanolamide | 0.6 g |
| Polydimethylsiloxane containing aminoethyl iminopropyl groups, as a cationic 35% emulsion in water, sold by the company Dow Corning under the name «DC 939", | 7 g |
| Sodium lauryl ether sulphate (2.2 EO) containing approximately 70% A.M. | 22 g |
| Terpolymer of acrylates, amino(meth)acrylates and $C_{10}$–$C_{30}$ alkyl itaconate, polyoxyethylenated with 20 mol of ethylene oxide, in the form of an aqueous dispersion containing 20% A.M., sold by the company National Starch under the name «Structure ® Plus» | 1 g |
| Preserving agents | qs |
| Sterilized demineralized water | qs 100 g |

The pH is adjusted to 5 with citric acid or sodium hydroxide.

After using this shampoo, wet hair is found to have softness and dried hair is found to have softness, sheen, a smooth feel, suppleness and good manageability.

EXAMPLE III
Shampoo

| | |
|---|---|
| Sodium N-cocoylamidoethyl-N-ethoxy-carboxymethylglycinate at 38% A.M., sold under the name «Miranol C2M Conc«  by the company Rhodia Chimie | 1.5 g |
| Cocoyl betaine as an aqueous 30% solution | 6 g |
| Coconut acid monoisopropanolamide | 1 g |
| Oxyethylenated laury alcohol (2.5 EO) | 0.75 g |
| Sodium lauryl ether sulphate (2.2 EO) containing 70% A.M. | 16.75 g |
| Distearyl ether | 1.5 g |
| Terpolymer of acrylates, amino(meth)acrylates and $C_{10}$–$C_{30}$ alkyl itaconate, polyoxyethylenated with 20 mol of ethylene oxide, in the form of an aqueous dispersion containing 20% A.M., sold by the company National Starch under the name «Structure ® Plus» | 2.5 g |
| Mixture of linear alcohols (C18/C20/C22) | 1.5 g |
| Fragrance, preserving agents | qs |
| Sterilized demineralized water | qs 100 g |

The pH is adjusted to 6.5 with citric acid or sodium hydroxide.

After using this shampoo, wet hair is found to have softness and dried hair is found to have softness, sheen, a smooth feel, suppleness and good manageability.

EXAMPLE IV
Shampoo

| | |
|---|---|
| Sodium chloride | 0.3 g |
| Vitamin B3 or PP: nicotinamide | qs |
| Sodium N-cocoylamidoethyl-N-ethoxy-carboxymethylglycinate (38%) | 1.5 g |
| Vitamin B6: pyridoxine hydrochloride | qs |
| Hydroxypropyl guar trimethyl ammonium chloride sold under the name «Jaguar C13S» by the company Meyhall | 0.04 g |
| Polydimethylsiloxane with a viscosity of 0.3 m².s⁻¹, sold under the | 1.8 g |

-continued

| | |
|---|---|
| «DC 200/300,000» by the company Dow Corning | |
| Oxyethylenated lauryl alcohol (2.5 EO) | 0.75 g |
| Fruit extracts in aqueous solution | qs |
| Coconut acid monoisopropanolamide | 2 g |
| Cocoyl amidopropyl betaine as an aqueous 38% solution | 2.7 g |
| Sodium lauryl ether sulphate (2.2 EO) at 70% | 17 g |
| Pyrus Malus (INCI) | qs |
| Distearyl ether | 1.5 g |
| Terpolymer of acrylates, amino(meth)acrylates and $C_{10}$–$C_{30}$ alkyl itaconate, polyoxyethylenated with 20 mol of ethylene oxide, in the form of an aqueous dispersion containing 20% A.M., sold by the company National Starch under the name «Structure ® Plus» | 1 g |
| Mixture of linear alcohols (C18/C20/C22) | 1.5 g |
| Fragrance, preserving agents | qs |
| Sterilized demineralized water | qs 100 g |

The pH is adjusted to 7.5 with citric acid or sodium hydroxide.

After using this shampoo, wet hair is found to have softness and dried hair is found to have softness, sheen, a smooth feel, suppleness and good manageability.

We claim:

1. A composition for washing keratin materials, comprising, in a cosmetically acceptable medium:
   I) at least one anionic, amphoteric or nonionic detergent surfactant;
   II) at least 1.5% by weight, relative to the total weight of the composition, of at least one nacreous and/or opacifying agent chosen from:
   i) esters of long-chain ($C_{10}$–$C_{30}$) monoalcohols and of long-chain ($C_{10}$–$C_{30}$) fatty acids;
   ii) long-chain ($C_{10}$–$C_{30}$) fatty alkyl ethers;
   iii) long-chain ($C_{10}$–$C_{30}$) esters of long-chain ($C_{10}$–$C_{30}$) alkanolamides;
   iv) N,N-dihydrocarbyl($C_{10}$–$C_{30}$)amidobenzoic acid and its salts;
   v) alcohols containing from 27 to 48 carbon atoms and comprising one or two ether and/or thioether or sulphoxide groups; and
   III) at least one acrylic terpolymer which contains, in amounts based on the total weight of monomers constituting the terpolymer:
   acrylate monomer (a), in amount of 5% to 80% by weight and selected from the group consisting of a $C_1$–$C_6$ alkyl acrylate and a $C_1$–$C_6$ alkyl methacrylate;
   monomer (b), in an amount of 5% to 80% by weight and selected from the group consisting of a heterocyclic vinyl compound containing at least one nitrogen or sulphur atom, a (meth) acrylamide, a mono- and di($C_1$–$C_4$) alkylamino($C_1$–$C_4$) alkyl (meth) acrylate, and a mono- and di($C_1$–$C_4$) alkylamino($C_1$–$C_4$) alkyl (meth) acrylamide; and
   monomer (c), in an amount of 0.1% to 30% by weight and selected from the group consisting of:
   i) a urethane produced by reaction between a monoethylenic unsaturated isocyanate and a nonionic surfactant encompassing a block copolymer of 1,2-butylene oxide and of ethylene oxide containing a $C_{1-4}$ alkoxy end;
   ii) a copolymerizable ethylenic unsaturated surfactant monomer obtained by condensing a nonionic surfactant with an α, β-ethylenic unsaturated carboxylic acid or its anhydride;
   iii) a urea surfactant monomer produced by reacting a monoethylenic unsaturated monoisocyanate with a nonionic surfactant containing an amine functionality;
   iv) a (meth) allyl ether of formula $CH_2=CR_1CH_2OA_mB_nA_pR_2$ in which $R_1$ denotes a hydrogen atom or a methyl group, A denotes propylenoxy or butylenoxy group, B denotes ethylenoxy, n is equal to zero or denotes an integer less than or equal to 200, m and p denote zero or an integer less than n, and $R_2$ is a hydrophobic group of at least 8 carbon atoms; and
   v) a nonionic urethane monomer produced by reacting a monohydric nonionic surfactant with a monoethylenic unsaturated isocyanate.

2. The composition according to claim 1, wherein the terpolymer is present in a proportion of 0.01% to 20% by weight relative to the total weight of the composition.

3. The composition according to claim 1, wherein the monomer (a) is a $C_2$–$C_6$ alkyl acrylate.

4. The composition according to claim 1, wherein the monomer (b) is N,N-dimethylaminoethyl methacrylate, N,N-diethylaminoethyl acrylate, N,N-diethylaminoethyl methacrylate, N-t-butylaminoethyl acrylate, N-t-butylaminoethyl methacrylate, N,N-dimethylaminopropylacrylamide, N,N-dimethylaminopropylmethacrylamide, N,N-diethylaminopropylacrylamide, or N,N-diethylaminopropylmethacrylamide.

5. The composition according to claim 1, wherein the monomer (c) is a copolymerizable ethylenic unsaturated surfactant monomer obtained by condensing a nonionic surfactant with itaconic acid.

6. The composition according to claim 1, wherein the acrylic terpolymer consists of acrylates, amino (meth) acrylates, and $C_{10}$–$C_{30}$ alkyl itaconate, polyoxyethylenated with 20 mol of ethylene oxide.

7. The composition according to claim 1, wherein the acrylic terpolymer further contains a crosslinking monomer.

8. The composition according to claim 1, wherein the nacreous and/or opacifying agent is selected from the group consisting of:
   i) esters of long-chain ($C_{10}$–$C_{30}$) monoalcohols and of long-chain ($C_{10}$–$C_{30}$) fatty acids;
   ii) long-chain fatty alkyl ethers that are solid at a temperature of less than or equal to 30° C.;
   iii) long-chain ($C_{10}$–$C_{30}$) esters of long-chain (C10–C30) alkanolamides;
   iv) N,N-dihydrocarbyl($C_{10}$–$C_{30}$) amidobenzoic acids and there salts; and
   v) alcohols containing from 27 to 48 carbon atoms and comprising one or two ether and/or thioether or sulphoxide groups, corresponding to formula (II):

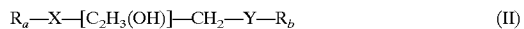

$$R_a—X—[C_2H_3(OH)]—CH_2—Y—R_b \qquad (II)$$

in which $R_a$ and $R_b$ denote, independently of each other, linear $C_{12}$ to $C_{24}$ groups; X denotes an oxygen atom, a sulphur atom, or a sulphoxide or methylene group; Y denotes an oxygen atom, a sulphur atom, or a sulphoxide or mehtylene group; the sum of the number of carbon atoms present in the groups $R_a$ and $R_b$ has a value ranging from 24 to 44 inclusive; when X or Y denotes sulphoxide, Y or X does not denote sulphur.

9. The composition according to claim 8, wherein the nacreous and/or opacifying agent is distearyl ether, or 1-(hexadecyloxy)-2-octadecanol.

10. The composition according to claim 1, wherein the anionic surfactants are selected from the group consisting of alkaline salts, magnesium salts, ammonium salts, amine salts, and amino alcohol salts of:

alkyl sulphates, alkyl ether sulphates, alkylamido ether sulphates, alkylaryl polyether sulphates, monoglyceride sulphates, alkyl sulphonates, alkylamide sulphonates, alkylaryl sulphonates, olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl phosphates, alkyl ether phosphates, acyl sarcosinates, acyl isethionates and N-acyl taurates,
wherein alkyl and acyl is carbon-based chain containing from 8 to 30 carbon atoms, fatty acid salts of oleic, ricinoleic, palmitic, or stearic acid; coconut oil acid or hydrogenated coconut oil acid; $C_8$–$C_{30}$ acyl lactylates; alkyl D-galactosiduronic acids or salts thereof, polyoxyalkylenated alkyl or alkylaryl ether carboxylic acids or salts thereof; or polyoxyalkylenated alkylamido ether carboxylic acids or salts thereof.

11. The composition according to claim 1, wherein the nonionic surfactants are polyethoxylated, polypropoxylated or polyglycerolated fatty acids or alkylphenols or alcohols having a fatty chain containing 8 to 30 carbon atoms, having between 2 and 50 ethylene oxide or propylene oxide groups, and having between 2 and 30 glycerol groups; copolymers of ethylene oxide and propylene oxide; condensates of ethylene oxide or propylene oxide with fatty alcohols; polyethoxylated fatty amides; polyglycerolated fatty amides; polyethoxylated fatty amines; oxyethylenated fatty acid esters of sorbitan; fatty acid esters of sucrose or of polyethylene glycol; alkylpolyglycosides; or carbamate or amide derivatives of N-alkylglucamines, aldobionamides, or amine oxides.

12. The composition according to claim 1, wherein the amphoteric surfactants are secondary or tertiary aliphatic amine derivatives, in which the aliphatic radical is a linear or branched chain containing 8 to 22 carbon atoms and which contains at least one carboxylate, sulphonate, sulphate, phosphate, or phosphonate water-solubilizing anionic group; ($C_8$–$C_{20}$)alkyl-betaines; sulpho-betaines; ($C_8$–$C_{20}$)alkylamido($C_1$–$C_6$)alkylbetaines; or ($C_8$–$C_{20}$)alkylamido ($C_1$–$C_6$)alkylsulphobetaines.

13. The composition according to claim 1, wherein the detergent surfactant is present in a proportion of at least 4% by weight relative to the total weight of the composition.

14. The composition according to claim 1, having a pH between 3 and 12.

15. The composition according to claim 1, wherein the cosmetically acceptable medium is water, one or more solvents, or of a mixture of water and at least one solvent selected from the group consisting of lower alcohols, alkylene glycols, and polyol ethers.

16. The composition according to claim 1, further comprising at least one volatile or non-volatile silicone selected from the group consisting of:
(i) polyalkylsiloxanes;
(ii) polyarylsiloxanes;
(iii) polyalkylarylsiloxanes;
(iv) silicone gums;
(v) silicone resins;
(vi) organomodified polyorganosiloxanes;
(vii) block copolymers containing a linear polysiloxane-polyalkylene block as a repeating unit;
(viii) grafted silicone polymers, containing a non-silicone organic skeleton;

(ix) grafted silicone polymers, containing a polysiloxane skeleton grafted with non-silicone organic monomers; and
(x) mixtures thereof.

17. The composition according to claim 16, wherein the at least one volatile or non-volatile silicone is present in a proportion between 0.01% and 20% by weight relative to the total weight of the composition.

18. The composition according to claim 1, further comprising at least one cationic polymer selected from the group consisting of proteins and protein hydrolysates, polyamine, polyaminoamide, and polyquaternary ammonium polymers, polyalkyleneimines, polymers containing vinylpyridine units, polymers containing vinylpyridinium units, condensates of polyamines and of epichlorohydrin, polyquaternary ureylenes, and chitin derivatives.

19. The composition according to claim 18, wherein the cationic polymer is present in a proportion between 0.001% and 20% by weight relative to the total weight of the composition.

20. The composition according to claim 1, further comprising at least one cosmetically acceptable adjuvant selected from the group consisting of fragrances, preserving agents, screening agents, sequestering agents, wetting agents, sugars, plant, animal, mineral and synthetic oils, amphoteric polymers, menthol, nicotinate derivatives, agents for preventing hair loss, foam stabilizers, propellants, dyes, ceramides, vitamins, provitamins, acidifying agents, and basifying agents.

21. In a shampoo, lotion, or conditioner the improvement wherein the shampoo, lotion, or conditioner contains the composition as defined in claim 1.

22. The composition according to claim 1, wherein the N,N-dihydrocarbyl($C_{10}$–$C_{30}$)amidobenzoic acid and its salts is a N,N-dihydrocarbyl($C_{12}$–$C_{22}$)amidobenzoic acid and its salts.

23. The composition of claim 1, wherein monomer (a) is present in an amount of 15% to 70% by weight.

24. The composition of claim 1, wherein monomer (a) is present in an amount of 40% to 70% by weight.

25. The composition of claim 1, wherein monomer (b) is present in an amount of 10% to 70% by weight.

26. The composition of claim 1, wherein monomer (b) is present in an amount of 20% to 60% by weight.

27. The composition of claim 1, wherein monomer (c) is present in an amount of 0.1% to 10% by weight.

28. The composition of claim 2, wherein the terpolymer is present in a proportion of 0.1% to 10% by weight relative to the total weight of the composition.

29. The composition of claim 3, wherein the monomer (a) is ethyl acrylate.

30. The composition of claim 4, wherein the monomer (b) is N,N-dimethylaminoethyl methacrylate.

31. The composition according to claim 8, wherein the esters iii) of long-chain ($C_{10}$–$C_{30}$) monoalcohols and of long-chain ($C_{10}$–$C_{30}$) fatty acids is cetyl palmitate.

32. The composition according to claim 8, wherein the long-chain fatty alkyl ethers that are solid at a temperature less than or equal to 30° C. are dialkyl ethers of formula(I):

$$R\!-\!\!O\!-\!\!R' \qquad\qquad (I)$$

in which R and R', which may be identical or different, denote a saturated or unsaturated, linear or branched alkyl radical containing from 10 to 30 carbon atoms, R and R' being chosen such that the compound of formula (I) is solid at a temperature of less than or equal to 30° C.

33. The composition according to claim 32, wherein R and R', which may be identical or different, denote a saturated or unsaturated, linear or branched alkyl radical containing from 14 to 24 carbon atoms.

34. The composition according to claim 8, wherein the long-chain ($C_{10}$–$C_{30}$) esters of long-chain ($C_{10}$–$C_{30}$) alkanolamides are stearamide diethanolamide distearate or stearamide monoethanolamide stearate.

35. The composition according to claim 22, wherein the N,N-dihydrocarbyl($C_{12}$–$C_{22}$)amidobenzoic acids are N,N-di($C_{16}$–C18) amidobenzoic acid.

36. The composition according to claim 1, wherein the nacreous and/or opacifying agent is present in a proportion between 1.5% and 20% by weight relative to the total weight of the composition.

37. The composition according to claim 1, wherein the nacreous and/or opacifying agent is present in a proportion between 2% and 6% by weight relative to the total weight of the composition.

38. The composition according to 18, wherein:
the proteins or protein hydrolysates are collagen hydrolysates bearing triethylammonium groups, collagen hydrolysates bearing trimethylammonium chloride or trimethylstearylammonium chloride groups, protein hydrolysates bearing on the polypeptide chain quaternary ammonium groups comprising at least one alkyl radical containing from 1 to 18 carbon atoms, or quaternized plant proteins; and
the polyamine, polyaminoamide, or polyquaternary ammonium polymers are
  i) quaternized or non-quaternized vinylpyrrolidone/dialkylaminoalkyl acrylate or methacrylate copolymers,
  ii) cellulose ether derivatives comprising quaternary ammonium groups,
  iii) cationic cellulose derivatives such as cellulose copolymers or cellulose derivatives grafted with a water-soluble quaternary ammonium monomer,
  iv) polysaccharides,
  v) polymers consisting of piperazinyl units and of divalent alkylene or hydroxyalkylene radicals containing straight or branched chains, optionally interrupted with oxygen, sulphur or nitrogen atoms or with aromatic or heterocyclic rings, or oxidation or quaternization products of said polymers,
  vi) water-soluble polyaminoamides,
  vii) polyaminoamide derivatives resulting from the condensation of polyalkylene polyamines with polycarboxylic acids followed by alkylation with bifunctional agents,
  viii) polymers obtained by reacting a polyalkylene polyamine comprising two primary amine groups and at least one secondary amine group with a dicarboxylic acid selected from the group consisting of diglycolic acid and saturated aliphatic dicarboxylic acids containing from 3 to 8 carbon atoms,
  ix) cyclopolymers of methyldiallylamine or of dimethyldiallylammonium,
  x) diquaternary ammonium polymers,
  xi) polyquaternary ammonium polymers,
  xii) homopolymers or copolymers derived from acrylic or methacrylic acids and comprising
    —$CH_2$—$CHR_a$—CO—O—$A_1$—$NR_eR_f$, $CH_2$—$CHR_a$—CO—O—$A_1$—$N^+R_bR_cR_d$ $X^-$, and/or $CH_2$—$CHR_{a-CO-NH-A_1}$—$N^+R_bR_cR_d$ $X^-$ units,
    in which $R_a$ independently denotes H or $CH_3$, $A_1$ independently denotes a linear or branched alkyl group of 1 to 6 carbon atoms or a hydroxyalkyl group of 1 to 4 carbon atoms, $R_b$, $R_c$ and $R_d$, which may be identical or different, independently denote an alkyl group of 1 to 18 carbon atoms or a benzyl radical, $R_e$ and $R_f$ represent a hydrogen atom or an alkyl group of 1 to 6 carbon atoms, $X^-$ denotes an anion,
  xiii) quaternary polymers of vinylpyrrolidone and of vinylimidazole,
  xiv) polyethylene glycol tallow polyamine, or
  xv) crosslinked methacryloyloxyethyltrimethylammonium chloride polymers.

39. A process for treating hair and/or scalp, comprising the step of applying to the hair and/or scalp, when wet or dry, at least one composition as defined in claim 1.

40. The process of claim 39, further comprising the step of rinsing the hair and/or scalp with water after the applying step.

41. The process of claim 40, further comprising the step of leaving the composition on the hair and/or scalp for a period of time before the rinsing step.

* * * * *